(12) United States Patent
Mabile et al.

(10) Patent No.: US 6,352,672 B1
(45) Date of Patent: Mar. 5, 2002

(54) APPARATUS FOR MEASURING THE LUMINESCENCE EMITTED IN A LUMINESCENT ASSAY

(75) Inventors: Michel Mabile, La Celle Saint Cloud; Gérard Mathis; Etienne Jean-Pierre Jolu, both of Bagnols sur Ceze; Dominique Pouyat, Roquemaure; Christophe Dumont, Thourotte, all of (FR)

(73) Assignee: CIS bio international (FR)

( * ) Notice: Subject to any disclaimer, the term of this patent is extended or adjusted under 35 U.S.C. 154(b) by 0 days.

(21) Appl. No.: 09/353,668

(22) Filed: Jul. 15, 1999

Related U.S. Application Data (60) Continuation of application No. 08/651,330, filed on May 22, 1996, now abandoned, which is a division of application No. 08/094,085, filed as application No. PCT/FR92/00069 on Jan. 27, 1992, now Pat. No. 5,527,684.

(30) Foreign Application Priority Data

Jan. 28, 1991 (FR) .............................................. 91 00930

(51) Int. Cl.[7] .............................................. G01N 21/64
(52) U.S. Cl. ................................. 422/82.08; 250/458.1
(58) Field of Search .......................... 422/82.05, 82.06, 422/82.07, 82.08; 436/172; 250/458.1, 459.1

(56) References Cited

U.S. PATENT DOCUMENTS

| | | | |
|---|---|---|---|
| 4,100,416 A | 7/1978 | Hirschfeld | 250/461 B |
| 4,341,957 A | 7/1982 | Wieder | 250/461.2 |
| 4,542,104 A | 9/1985 | Stryer et al. | 436/536 |
| 4,792,689 A | 12/1988 | Peterson | 250/458.1 |
| 4,868,103 A | 9/1989 | Stavrianopoulos et al. | 435/5 |
| 4,876,190 A | 10/1989 | Recktenwald | 435/7 |
| 5,383,023 A | 1/1995 | Walleczek | 356/417 |
| 5,527,684 A | 6/1996 | Mabile et al. | 435/7.1 |

FOREIGN PATENT DOCUMENTS

| | | |
|---|---|---|
| EP | 0 266 881 A3 | 5/1988 |
| EP | 0 278 149 A3 | 8/1988 |
| GB | 2 215 838 A | 9/1989 |
| GB | 2 228 081 A | 8/1990 |

OTHER PUBLICATIONS

Collins, W.P. (ed.) *Alternative Immunoassays*, John Wiley & Sons, Ltd., 1985, 103–217.

Primary Examiner—Jeffrey Snay
(74) Attorney, Agent, or Firm—Woodcock Washburn LLP (57) ABSTRACT

The present invention relates to an apparatus for measuring the luminescence emitted in a luminescent assay, which makes it possible to correct certain perturbations due to the measuring medium.

19 Claims, 3 Drawing Sheets

APPARATUS FOR MEASURING THE LUMINESCENCE EMITTED IN A LUMINESCENT ASSAY

CROSS-REFERENCE TO RELATED APPLICATIONS

This Application is a continuation of application Ser. No. 08/651,330 filed May 22, 1996, now abandoned, which is a divisional of application Ser. No. 08/094,085 filed Jul. 28, 1993, now U.S. Pat. No. 5,527,684, which is the National Stage of International Application Serial No. PCT/FR92/00069 filed Jan. 27, 1992.

The invention relates to a method of measuring the luminescence emitted in a luminescent assay, which makes it possible to correct certain perturbations due to the measuring medium.

At the present time, immunoassays are widely used for the qualitative and quantitative analysis of compounds in biological fluids.

Among the techniques in existence, fluorimetric assays have become increasingly important.

In fact, they have a number of advantages, including the sensitivity and rapidity of the measurement, the stability and safety of the reagents labeled with fluorescent compounds, and the relatively low cost.

It is known that detection methods which use fluorescence are intrinsically very sensitive and could permit lower detection limits than those achieved by immunoassays which use radiolabeled reagents, in particular if modulatable laser light sources are used (I. Wieder, Immunofluorescence and related staining techniques, 1978, Elsevier).

Numerous fluorescent molecules usable as tracers in assays of this type have previously been described; among these, rare earth complexes, which possess valuable properties, may be mentioned in particular.

"Tracer" is understood as meaning either a luminescent molecule emitting a direct luminescence, or a luminescent molecule capable of inducing a luminescent emission, it being possible for said molecule to be coupled with one of the reagents of the assay, and the emission of a direct or induced luminescence enabling the target analyte to be detected and/or determined.

The use of particular complexes, rare earth cryptates, is described for example in European patent applications 0 321 353, 0 180 492 and 0 232 348 or international patent application WO 90/04791.

These rare earth cryptates have the advantage of being very stable in a saline protein medium, this property being particularly important in the case of homogeneous immunoassays.

The sensitivity of the measurement is nevertheless limited by different interference parameters, among which the following may be mentioned:

the spectroscopic properties of the medium, and in particular its intrinsic fluorescence, which is due especially to the interference emissions of the molecules present in the measuring medium and capable of being excited and of emitting at wavelengths close to those of the fluorescent tracer and/or with strong intensities; its absorption, which results in a loss of exciting light; and its light diffusion properties when the measuring medium is not clear;

the quenching of the emitted fluorescence by inhibitors present in the medium; and the composition of the equipment, and especially the interference reflections caused by the equipment.

Together these interferences considerably affect the sensitivity and reproducibility of the measurement.

Some of these problems have already been solved by a variety of techniques.

In particular, the time-resolved methods of measuring fluorescence enable the problem of interference emissions (background) to be partially overcome. The principle of these methods consists in measuring the fluorescence emitted by a tracer molecule having a relatively long emission lifetime, the measurement being delayed in time beyond the emission lifetime of the other molecules present.

It is necessary in this case to use fluorescent tracer molecules with a relatively long lifetime, such as rare earth chelates and cryptates.

Nevertheless, the problem of the limitations due to the spectroscopic properties of the medium, and in particular to its absorption, has not been solved satisfactorily.

In fact, none of the proposed techniques for avoiding the filtering effect of the medium makes it possible to carry out the measurement easily and inexpensively and at the same time to obtain a high sensitivity and a very good reproducibility in the measurement.

In particular, the solution which consists in greatly diluting the sample detracts from the sensitivity of the detection.

Furthermore, the use of a double exciting beam system involves the use of expensive equipment and special measuring cuvettes which are difficult to standardize. Moreover, systematic measurement of the absorption of the medium prior to measurement of the fluorescence of the sample complicates the assay method.

European patent application 355 849 describes a method and an automatic apparatus for checking the reliability of the fluorescent measurement of a sample and for correcting this measurement on the basis of an internal reference. To do this, measurement of the test sample has to be preceded by a measurement with 2 reference samples, one being a "blank" containing only the measuring medium, and the other containing the measuring medium and the fluorescent marker.

European patent application 91 126 relates to a fluorimeter which makes it possible to measure, in parallel with the fluorescence of the sample, the transmission of the sample and the fluctuations in excitation energy, in order to correct the measured fluorescence. This system requires a particular measuring cell which allows the exciting beam to pass through, since the transmission measurement has to be made in line with the exciting beam.

Other systems employ a system for splitting the exciting beam, as described for example in European patent applications 174 722 and 241 268.

The invention therefore relates to a method of measuring the luminescence emitted in a luminescent assay, which comprises employing at least one luminescent tracer compound and a luminescent compound used as an internal reference, which, when exposed to the same excitation wavelength, are capable of emitting at different wavelengths, $\lambda_2$ and $\lambda_1$ respectively, either by direct luminescence or by the induction of a luminescent emission, the luminescence of the reference compound reflecting the optical quality of the medium, and correcting the measurement of the luminescence emitted by the tracer compound at wavelength $\lambda_2$ on the basis of the measurement of the luminescence emitted by the reference compound at wavelength $\lambda_1$.

"Reference compound" is understood as meaning either a luminescent molecule emitting a direct luminescence, or a luminescent molecule capable of inducing a luminescent emission, said emission of a direct or indirect luminescence not being perturbed by the reagent system of the assay.

The luminescent compounds which can be used in the method of measurement according to the invention can emit directly either at their emission wavelength or at another wavelength, as for example in the case of a spectral shift associated with the reagent system of the assay.

If appropriate, the luminescent compounds which can be used in the method of measurement according to the invention can emit indirectly by inducing a luminescent emission, especially as in the case of homogeneous energy transfer methods.

Advantageously, the luminescent emissions at wavelengths $\lambda_2$ and $\lambda_1$ are detected simultaneously.

The method according to the invention, which uses a single exciting beam, permits easy and reliable measurement of the luminescence emitted in a luminescent assay without the need for complex equipment, by eliminating the perturbations due to the spectroscopic properties of the assay medium.

Advantageously, the emission wavelengths of the luminescent tracer compound and luminescent reference compound, $\lambda_2$ and $\lambda_1$, will be different but preferably similar (the difference being less than or equal to 100 nm, for example) so that the perturbation of the luminescent emission which is due to the absorption of the medium is produced in the same manner as regards the emission of the tracer compound and that of the reference compound.

It is pointed out that, advantageously, the method according to the present invention does not require the assay sample to be placed in a special measuring cell.

The luminescent emission of the reference compound at wavelength $\lambda_1$ enables the measurement made at wavelength $\lambda_2$ to be corrected. The correction can be effected for example by dividing the latter measurement by the measurement made at wavelength $\lambda_1$ Other means of correction can be used, for example a correction method, built into the apparatus, which consists in fixing a counting rate on the channel measuring the luminescent emission of the reference compound at wavelength $\lambda_1$. When this rate is reached, the end of the measurement on the channel measuring the luminescent emission at wavelength $\lambda_2$ is triggered. The value obtained on this channel is thereby corrected directly.

Other correction methods known to those skilled in the art can also be used.

According to a preferred feature, the invention relates to a method of measuring the fluorescence emitted in a fluorometric assay, which comprises employing at least one fluorescent tracer compound and a fluorescent compound used as an internal reference, which, when exposed to the same excitation wavelength, are capable of emitting at different wavelengths, $\lambda_2$ and $\lambda_1$ respectively, either by direct fluorescence or by the induction of a fluorescent emission, the fluorescence of the reference compound reflecting the optical quality of the medium, and the measurement of the fluorescence emitted by the tracer compound then being corrected on the basis of the measurement of the fluorescence emitted by the reference compound.

The method according to the invention makes it possible to achieve a measuring sensitivity of the order of picomol/liter, whereas the phenomena referred to above usually limit the sensitivity of the assay, especially in the case of homogeneous assays in a serum medium, to analyte concentrations of the order of micromol/liter.

According to an advantageous feature of the invention, the luminescent tracer compound and the reference compound are one and the same compound.

This first variant of the method according to the invention preferably applies when using a homogeneous luminescent method of detecting and/or determining an analyte in a medium in which it may be present, where the measurement of the emitted luminescence representing the quantity of analyte in the medium is made at a different emission wavelength from that of the tracer compound.

This case arises for example when the emitted luminescence representing the analyte results from an energy transfer between a luminescent donor compound and a luminescent acceptor compound, the latter emitting at a wavelength $\lambda_2$ and the donor compound, which also serves as the reference compound, emitting at a wavelength $\lambda_1$.

In particular, this case also arises when the tracer compound emits at different wavelengths $\lambda_1$ and $\lambda_2$ according to whether it does not or, respectively, does form part of the reagent system of the assay.

"Homogeneous method" is understood as meaning an assay method in which the measurement does not require the prior separation of the constituents of the assay.

Surprisingly, it has in fact been found that the intensity of the signal emitted by the luminescent reference compound at wavelength $\lambda_1$ is practically constant. The emitted signal is therefore a function only of the optical properties of the medium in which the assay is performed, and not of the quantity of analyte, and can serve as a reference.

In the case of a luminescent emission resulting from an energy transfer, the signal reflecting both the quantity of analyte to be assayed and the optical properties of the measuring medium is detected at a wavelength $\lambda_2$ and corrected on the basis of the measurement made at wavelength $\lambda_1$.

Preferably, this first variant of the method according to the invention will be used in a homogeneous luminescent method of detecting and/or determining an analyte in a medium in which it may be present, with the aid of an excess method consisting in:

1) adding to said medium containing the target analyte, a first reagent made up of at least one receptor for said analyte, coupled with a luminescent donor compound, 2) adding a second reagent made up of one or more other receptors for said analyte, said second reagent being coupled with a luminescent acceptor compound, 3) incubating said medium after the addition of each reagent or after the addition of both reagents, 4) exciting the resulting medium at the excitation wavelength of the luminescent donor compound, and 5) measuring the signal of the luminescent donor compound at a wavelength $\lambda_1$ this measurement serving as a reference, and the signal resulting from the energy transfer at a different wavelength $\lambda_2$.

According to an advantageous feature, the first and second reagents used in the above-indicated luminescent methods of detecting and/or determining an analyte are added simultaneously to the medium containing the target analyte.

According to another feature of the invention, this variant of the method can be used in a homogeneous luminescent method of detecting and/or determining an analyte in a medium in which it may be present, with the aid of a competitive method consisting in:

1) adding, to said medium containing the target analyte, a first reagent made up of at least one receptor for said analyte, coupled with a luminescent donor compound, 2) adding a second reagent made up of the analyte coupled with a luminescent acceptor compound, 3) incubating said medium after the addition of each reagent or after the addition of both reagents, 4) exciting the resulting medium at the excitation wavelength of the luminescent donor compound, and 5) measuring the signal of the luminescent donor compound at a wavelength $\lambda_1$ this measurement serving as a reference, and the signal resulting from the energy transfer at a different wavelength $\lambda_2$.

This variant of the method can also advantageously be used in a homogeneous luminescent method of detecting and/or determining an analyte in a medium in which it may be present, with the aid of a competitive method consisting in:

1) adding, to said medium containing the target analyte, a first reagent made up of at least one receptor for said analyte, coupled with a luminescent acceptor compound, 2) adding a second reagent made up of the analyte coupled with a luminescent donor compound, 3) incubating said medium after the addition of each reagent or after the addition of both reagents, 4) exciting the resulting medium at the excitation wavelength of the luminescent donor compound, and 5) measuring the signal of the luminescent donor compound at a wavelength $\lambda_1$, this measurement serving as a reference, and the signal resulting from the energy transfer at a different wavelength $\lambda_2$.

In another advantageous use of the method of the invention, at least one of the receptors for the analyte is bound to a solid support.

According to another advantageous feature, the luminescent tracer compound and the reference compound are 2 different compounds excitable at the same wavelength, the reference compound emitting at a different wavelength from that used to measure the quantity of analyte.

This second variant of the method of the invention is preferred in particular in the use of a homogeneous luminescent method of detecting and/or determining an analyte in a medium in which it may be present, said method using a reagent coupled with a luminescent tracer compound and a reagent coupled with a heavy atom, or moieties containing a heavy atom, capable of modulating the signal of the luminescent tracer compound. An assay method of this type is described in European patent application 232 348.

In this case, in addition to the luminescent tracer compound coupled with the receptor for the analyte and emitting at a wavelength $\lambda_2$, another, free luminescent compound, serving as a reference and emitting at a wavelength $\lambda_1$, will be used whose signal is not modulated by the heavy atom effect and reflects the optical properties of the measuring medium, these 2 compounds being excited at the same wavelength.

Advantageously, this second variant of the method according to the invention is used in a homogeneous luminescent method of detecting and/or determining an analyte in a medium in which it may be present, consisting in:

1) adding to said medium a first reagent made up of a receptor for said analyte, 2) adding a second reagent selected from the analyte or at least one of its receptors, one of the two reagents being coupled with a luminescent tracer compound and the other reagent containing a heavy atom or moieties containing a heavy atom, as well as a luminescent compound serving as an internal reference, 3) incubating the resulting medium either after the addition of each reagent or after the addition of both reagents, 4) exciting the resulting medium, and 5) measuring on the one hand the signal emitted by the luminescent tracer compound, said signal being modulated by the heavy atom effect at a wavelength $\lambda_2$, and on the other hand the signal emitted by the reference compound at a wavelength $\lambda_1$.

This second variant of the method, in which the luminescent tracer compound and the reference compound are two different compounds, can also advantageously be used in homogeneous methods of detecting and/or determining an analyte in a medium in which it may be present, with the aid of excess or competitive methods involving a donor/acceptor system, such as those described above for the first variant of the method of the invention.

Nevertheless, in the case of the second variant, a luminescent compound serving as an internal reference should be added during one of the reagent addition steps.

The signal of the luminescent reference compound will then be measured at a wavelength $\lambda 1$ and the signal resulting from the energy transfer will be measured at a wavelength $\lambda_2$, it then being possible for this measurement to be corrected on the basis of the measurement made at $\lambda_1$.

In the present description:

"analyte" defines any substance or group of analogous substances to be detected and/or determined;

"receptor" defines any substance capable of binding specifically to a site on said analyte;

"heavy atom" defines an atom of high atomic number whose presence in the proximity of a fluorescent molecule is capable of inducing an increase in the spin-orbit coupling of the latter; examples which may be mentioned of appropriate heavy atoms are especially halogen atoms, mercury, thallium, lead and silver;

"moiety containing at least one heavy atom" defines any chemical substance which naturally contains at least one heavy atom or to which at least one heavy atom can be bound.

According to a preferred feature, the measuring medium is a biological medium such as a serum medium.

Fluorescent compounds will advantageously be used as luminescent reference compounds and/or luminescent compounds usable as tracer compounds.

In particular, a fluorescent compound such as a rare earth chelate or cryptate will advantageously be used, especially a terbium, europium, dysprosium, samarium or neodymium chelate or cryptate. A terbium or europium cryptate will preferably be used.

In the fluorescent methods of detection and/or determination using the method of measurement of the invention, a rare earth cryptate described in European patent applications 180 492 and 321 353 will advantageously be chosen.

The terbium cryptate Tb trisbipyridine or the europium cryptate Eu trisbipyridine, as described in European patent application 180 492, or the cryptates Eu trisbipyridinediamine and Tb trisbipyridinediamine, described in European patent application 321 353, will preferably be used.

According to an advantageous feature, the fluorescent donor compound is a europium cryptate and the fluorescent acceptor compound is selected from allophycocyanin, allophycocyanin B, phycocyanin C or phycocyanin R.

It is also possible to use a phosphorescent compound, such as eosin or erythrosin, as the luminescent reference compound or donor tracer compound. In this case, it will be advantageous to use a fluorescent acceptor compound selected from chlorophylls such as those mentioned in European patent applications 71 991 and 314 406, or porphyrins such as those mentioned in European patent application 71 991, or else phthalocyanins such as those of international patent application WO 88 04777.

In the case of an assay in a liquid medium using phosphorescent donor compounds, the result will be read either from a solid support or by adding oxygen-capturing molecules to the measuring medium, these techniques being known to those skilled in the art.

Chlorophylls and phthalocyanins can also be used as fluorescent acceptor compounds, a europium cryptate or chelate being used as the donor compound.

According to a preferred feature, the luminescent tracer compound and/or the luminescent reference compound have a lifetime of more than one microsecond.

A modulatable light source, such as those described in Lakowicz, Principles of fluorescent spectroscopy, Plenum Press, New York, 1983, pp. 96–100, will advantageously be used as the light source permitting the excitation of the luminescent tracer and reference compounds.

The method of measurement of the invention has an important application in particular in fluorescent immunoassays, in both the so-called competitive and excess assay methods, which have been described in the prior art (Landon, Ann. Clin. Biochem., 1981, 18, 253, and E. SOINI et al., Clin. Chem., 1979, 25, 353).

In particular, the method of measurement of the invention can advantageously be used in immunoassays in a serum medium.

A further feature of the invention relates to a device for carrying out the method of measurement according to the invention.

This device comprises an exciting light source, means for collecting the light beam emitted following said excitation, and means for measuring the luminescence at two different wavelengths.

Advantageously, this device also comprises means for splitting the beam emitted following excitation.

Figure 1:
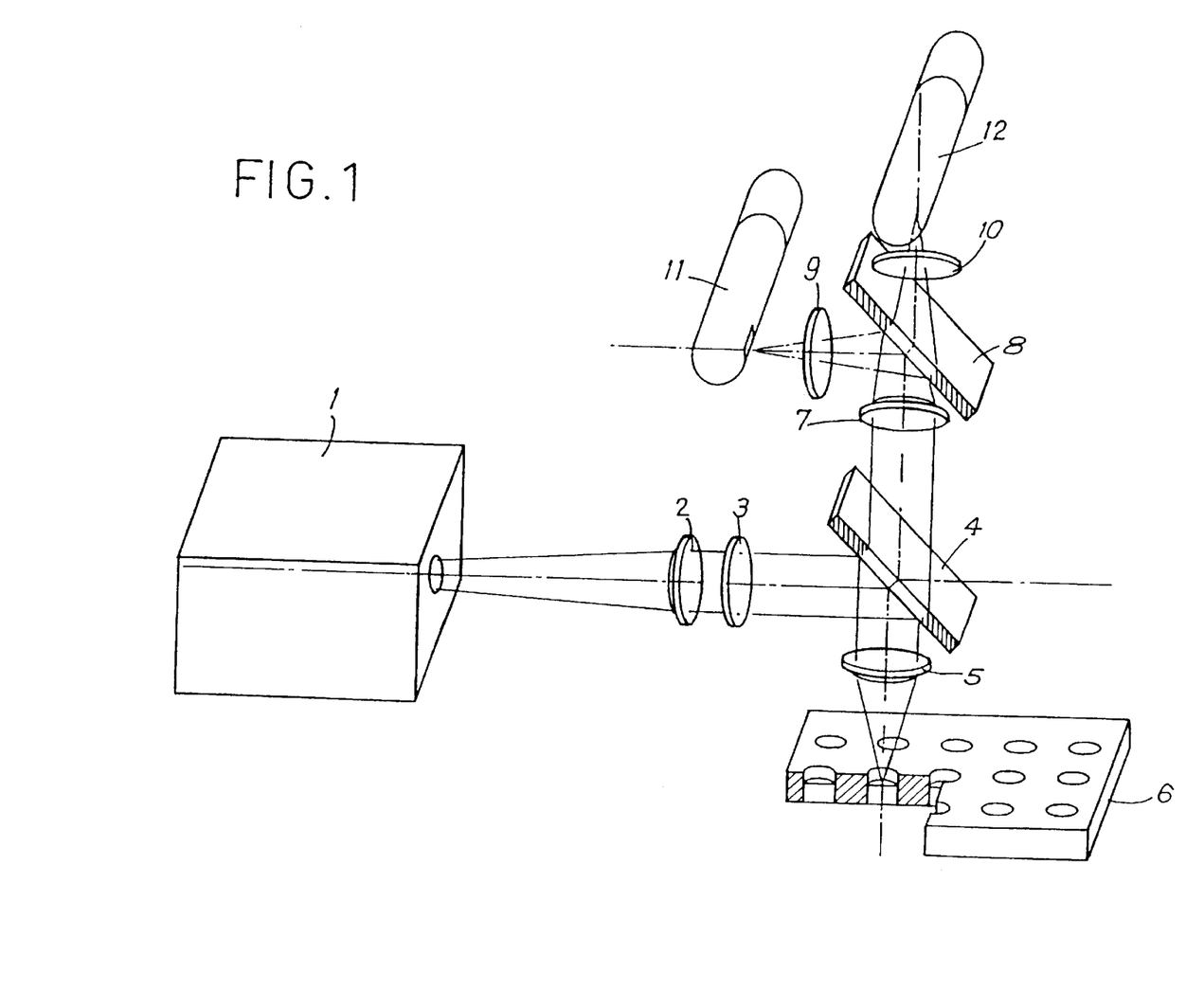
FIG. 1 is a schematic illustration of a system for practicing the invention.

Such a device is illustrated by way of example in FIG. 1.

FIG. 1 shows:

an exciting light source 1;

a lens 2, which focuses the exciting beam towards a filter 3 for selecting the desired excitation wavelength;

a dichroic filter 4 arranged at 45°, for reflecting the ultraviolet rays and transmitting the visible light, which reflects the exciting beam on to a lens 5, the latter focusing it on to the microplate 6 containing the samples;

a lens 7, which, in combination with the lens 5, collects the luminescent emission resulting from the excitation and projects it on to a dichroic filter 8, which splits the emitted light beam; and filters 9 and 10, which select the signals emitted by the reference compound and tracer compound before they arrive at photomultipliers 11 and 12.

The invention will be understood more clearly with the aid of the Examples below, which in no way imply a limitation.

EXAMPLE 1

Correction of fluorescence at 665 nm by the detection of an added terbium cryptate (trisbipyridine-diamine ($Tb^{3+}$)) in a homogeneous fluorescent immunoassay of prolactin This Example is carried out on the detection of a standard antigen range and on the assay of 5 serum samples of unknown prolactin concentration.

Methodology

This assay uses as the fluorescent donor compound the europium cryptate trisbipyridinediamine ($Eu^{3+}$) (tracer) and as the reference compound the terbium cryptate trisbipyridinediamine ($Tb^{3+}$), both prepared as described in European patent application 321 353 (Examples 3 and 4).

Allophycocyanin (Cyanotech, USA) is used as the fluorescent acceptor compound.

Anti-prolactin $E_1$ and 3D3 monoclonal antibodies (CIS bio international, France), recognizing 2 different epitopes of prolactin, are used. The preparation of the antibodies labeled with the europium cryptate trisbipyridinediamine ($Eu^{3+}$) or with allophycocyanin is described below:

The following abbreviations are used:

APC=allophycocyanin

DTT=dithiothreitol

Eu TBP=europium cryptate trisbipyridinediamine ($Eu^{3+}$)

HSA=human serum albumin

IgG=immunoglobulin G

SPDP=N-succinimidyl 3-(2-pyridyldithio) propionate

Sulfo-SMCC=sulfosuccinimidyl 4-(N-maleimidomethyl) cyclohexane-1-carboxylate

1) Preparation of IgG $E_1$/APC a) Activation of APC With Sulfo-SMCC

APC (3 mg), supplied commercially in precipitated form in a 60% solution of ammonium sulfate, is centrifuged. After removal of the supernatant, the residue is taken up in 250 $\mu$l of 100 mM phosphate buffer, pH 7.0, and then passed through a 0.8 $\mu$m filter to remove any suspended particles.

The filtrate is purified by exclusion chromatography on a G25 superfine column (Pharmacia, Sweden) in the same buffer. The concentration of APC eluted in the exclusion volume is determined at 650 nm with $\epsilon_{650}$ nm=731,000 $M^{-1}$ $cm^{-1}$.

The APC is activated by adding a freshly prepared solution of sulfo-SMCC at a concentration of 6.9 mM in 100 mM phosphate buffer, pH 7.0, and by allowing the reaction to proceed for one hour at room temperature, with gentle stirring (molar ratio of 15 to 75 sulfo-SMCC per APC). The APC-maleimide is then purified on a G25 superfine column in 100 mM phosphate buffer, EDTA 5 mM, pH 6.5, and kept at 4° C. prior to coupling with IgG 3D3.

b) Activation of IgG $E_1$ With SPDP

Simultaneously, 5 mg of IgG $E_1$, at a concentration of 10 mg/ml in 100 mM phosphate buffer, pH 7.0, are activated by the addition of a solution of SPDP (Pierce, USA), at a concentration of 6.4 mM in dioxane, in a molar ratio of 4 to 16 SPDP per IgG $E_1$.

After activation for 35 min at room temperature, the IgG-pyridine-2-thione is purified on a G25 superfine column in 100 mM phosphate buffer, EDTA 5 mM, pH 6.5.

The proteins are concentrated and the 2-pyridyl disulfide groups are reduced with a solution of DTT (Sigma, USA), having a final concentration of 19 mM, for 15 min at room temperature. The DTT and pyridine-2-thione are removed by purification on a G25 superfine column in 100 mM phosphate buffer, EDTA 5 mM, pH 6.5. The concentration of IgG-SH is determined at 280 nm with $E_{280\ nm}$=210,000 $M^{-1}$ $cm^{-1}$.

c) Conjugation of IgG $E_1$-SH With APC-maleimide

The thiol groups are bound to the maleimides by adding 2.51 mg of activated APC per mg of IgG $E_1$. After incubation for 18 hours at 4° C. in the dark, with gentle stirring, the thiol groups which have remained free are blocked by the addition of a 100 mM solution of N-methylmaleimide (Sigma, USA), having a final concentration of 20 mM, for one hour at room temperature.

The reaction medium is purified by gel filtration on a TSK G3000SW semipreparative column (Beckmann, USA) in 100 mM phosphate buffer, pH 7.0.

The concentrations of APC and IgG $E_1$ in the purified conjugate eluted in the first peak are determined by the absorptions at 280 nm and 650 nm according to the following calculation:

[APC]$_{mol/l}$=A$_{650nm}$/710,000

[IgG]$_{mol/l}$=(A$_{280nm}$-A'$_{280nm}$)/210,000 where A'$_{280nm}$ is the contribution of the APC-maleimide at this wavelength.

Human serum albumin (HSA) is added at a rate of 1 g/l to the conjugate, which is then divided up into aliquots and subsequently frozen at −20° C.

2) Preparation of IgG 3D3/Eu TBP Conjugates

IgG 3D3-SH is prepared according to the protocol described above for IgG $E_1$, but with a molar ratio of 7.5 SPDP per IgG 3D3.

A 25 mM solution of sulfo-SMCC in 20 mM phosphate buffer, dimethylformamide 10% (v/v), pH 7.0, is added to 5 mg ($5.10^{-6}$ mol) of Eu TBP in a proportion of 2.5 mol of activator per mol of Eu TBP.

After activation for 45 min at room temperature, the reaction medium is passed through a 0.8 μm filter to remove any precipitate formed. The unwanted reaction products (sulfo-SMCC, N-hydroxy succinimide, (N-maleimidomethyl)carboxylic acid) are removed by ion exchange chromatography on a Mono Q column (Pharmacia, Sweden) in 20 mM phosphate buffer, dimethylformamide 10% (v/v), pH 7.0, under NaCl shock. The concentration of Eu TBP-maleimide is determined at 307 nm with $\epsilon_{307nm}$=25,000 M$^{-1}$ cm$^{-1}$, and the ratio A$_{307nm}$/A$_{280nm}$ is also determined.

In a manner similar to that described above, the maleimide groups are reacted with the thiol groups bound to the antibody, in molar proportions varying from 10 to 30 Eu TBP-maleimide per IgG 3D3-SH.

After incubation for 18 hours at 4° C. and blocking of the thiol groups (which may have remained free) with N-methylmaleimide, the non-coupled Eu TBP is removed by dialysis in 100 mM phosphate buffer, pH 7.0, at 4° C. to the point of exhaustion (no more fluorescence in the dialysis baths).

The characteristics of the conjugate are determined by its absorptions at 307 nm and 280 nm using the following values, taking into account the inherent absorption of the cryptate determined by the ratio A$_{307nm}$/A$_{280nm}$.

Eu TBP-maleimide $\epsilon_{307nm}$=25,000 M$^{-1}$ cm$^{-1}$

A$_{307nm}$/A$_{280nm}$: determined experimentally

IgG 3D3-SH $\epsilon_{280nm}$=210,000 M$^{-1}$ cm$^{-1}$ $\epsilon_{307nm}$=0 M$^{-1}$ cm$^{-1}$ 3) The Following Are Introduced Successively Into 12-Well Strips (Microstrip Labsystem Oy, Finland)

100 μl of standard (prolactin standards from the ELSA-PRL kit (CIS Bio international) in newborn calf serum) or 100 μl of assay sample (human serum), 100 μl of anti-prolactin 3D3 monoclonal antibody labeled with the europium cryptate trisbipyridinediamine (Eu$^{3+}$), at a concentration of 0.5 g/ml of antibody in 100 mM phosphate buffer, NaF 150 mM, BSA (bovine serum albumin) 1 g/l, pH 7.0, 50 μl of anti-prolactin $E_1$ monoclonal antibody labeled with allophycocyanin, at a concentration of 7 μg/ml of antibody in 100 mM phosphate buffer, NaF 150 mM, BSA 1 g/l, pH 7.0, and 50 μl of the terbium cryptate trisbipyridinediamine (Tb$^{3+}$), $10^{-7}$M in 100 mM phosphate buffer, NaF 150 mM, BSA 1 g/l, pH 7.0.

After incubation for one hour at 37° C., the fluorescence of each well is measured according to two protocols:

In a first protocol, the fluorescence at 665 nm is detected by the time-resolved method with a measuring delay of 50 μs and an integration time of 400 μs. The measuring time is 1 s. The excitation is caused by a flashlamp pulsed at 1000 Hz. The excitation wavelength is centered by an interference filter at 307 nm, which is the absorption maximum of trisbipyridinediamine (Eu$^{3+}$) and trisbipyridinediamine (Tb$^{3+}$). The recorded intensity of fluorescence, which is a reflection of the energy transfer, is proportional to the concentration of prolactin antigen present in the incubation medium.

The measurement is made by means of an ARCUS fluorimeter (LKB, Sweden) using an interference filter adapted to the emission of the fluorescent acceptor compound and the reference compound.

It is also possible to make the measurement in a single step using the prototype fluorimeter described in Example 2. In this case, a 96-well white microplate (Dynatech, USA) will be used for the measurement.

The standard curve FLUO$_{665nm}$=f ([prolactin]) is plotted and the concentration of the 5 samples is measured.

The results are reported in Table I below:

TABLE I

| ELSA-PRL standard | [Prolactin] μIU/ml |
|---|---|
| STD$_0$ | 0 |
| STD$_1$ | 165 |
| STD$_2$ | 300 |
| STD$_3$ | 920 |
| STD$_4$ | 3100 |
| STD$_5$ | 6500 |
| Assay serum | [Prolactin] (FLUO$_{665}$) μIU/ml |
| Sam1 | 141 |
| Sam2 | 951 |
| Sam3 | 113 |
| Sam4 | 287 |
| Sam5 | 699 |

In a second protocol, the fluorescence at 665 nm is measured in the same way as described above. However, a second measurement of the same well is made at 545 nm after a second excitation, with the same temporal reading parameters (delay, integration time and measuring time). The fluorescent emission thus measured by the time-resolved method at 545 nm is characteristic of the emission of the trisbipyridinediamine (Tb$^{3+}$) used as the internal reference and reflects the optical properties of the assay medium.

The standard curve FLUO$_{665nm}$/FLUO$_{545nm}$=f ([prolactin]) is plotted and the concentration of the 5 samples is measured.

The results are reported in Table II below:

TABLE II

| ELSA-PRL standard | [Prolactin] µIU/ml |
|---|---|
| $STD_0$ | 0 |
| $STD_1$ | 165 |
| $STD_2$ | 300 |
| $STD_3$ | 920 |
| $STD_4$ | 3100 |
| $STD_5$ | 6500 |

| Assay serum | [Prolactin] ($FLUO_{665}/FLUO_{545}$) µIU/ml |
|---|---|
| Sam1 | 580 |
| Sam2 | 428 |
| Sam3 | 417 |
| Sam4 | 71 |
| Sam5 | 2044 |

Finally, as a reference, the 5 samples are also assayed by the ELSA-PRL radioimmunometric assay kit (CIS bio international, France).

The comparisons of the results of assays performed on the five samples are collated in Table III below:

TABLE III

| | [Prolactin] µIU/ml | | |
|---|---|---|---|
| | ELSA-PRL | $FLUO_{665}$ | $FLUO_{665}/FLUO_{545}$ |
| Sam1 | 612 | 141 | 580 |
| Sam2 | 395 | 951 | 428 |
| Sam3 | 425 | 113 | 417 |
| Sam4 | 59 | 287 | 71 |
| Sam5 | 1870 | 699 | 2044 |

These results show that the measurements of the concentrations of the prolactin samples by the method comprising a correction of the intensity of fluorescence ($FLUO_{665}/FLUO_{545}$) correlate well with the results obtained using the ELSA-PRL radioimmunometric assay, whereas this is not the case when the concentration is measured only by the intensity of fluorescence at 665 nm without correction ($FLUO_{665}$).

EXAMPLE 2

Correction of fluorescence at 665 nm by detection of the fluorescence of the antibody/cryptate conjugate at 620 nm in a homogeneous fluorescent immunoassay of prolactin The fluorescence is measured with the aid of a prototype fluorimeter, which is described below:

An N2 VSL 337 laser (LSI, USA) is used as the exciting source (wavelength at 337 nm). The pulse duration is specified at 3 nanoseconds and is repeated at a frequency of 10 Hertz. The beam passes through a filter (CORNING) to remove any light interfering with the excitation, other than 337 nm.

After entering the measuring chamber, the beam is reflected by a dichroic filter arranged at 45°, which has the property of reflecting the ultraviolet and of being able to transmit the visible light.

The beam reflected by the dichroic filter is focused by a fused silica lens on to the well to be measured in a microplate. The fluorescent emission is collected at a solid angle of 20°, collimated by the same lens, and passes directly through the dichroic filter (visible light fluorescence).

An interference filter, the characteristics of which are defined according to the fluorescent wavelength to be detected, makes it possible to remove the light capable of interfering with the signal, the intensity of which is then measured by a photomultiplier (HAMAMATSU R2949).

The photon counter used is an SR-400 (STANFORD RESEARCH SYSTEMS), whose operations and synchronization with the laser are controlled by a computer of the IBM PC-AT type via an RS 232 output. The pulses coming from the photomultiplier are recorded over a given time window ($t_g$) and after a given delay ($t_d$), provided they are above a discriminant level selected by the photon counter so as to optimize the signal-to-noise ratio of the photomultiplier.

An X-Y table, driven by the IBM PC-AT, uses step motors to set up the different positions. of the measuring microplate, including the maneuvers of charging, positioning under the exciting beam, automatic sequential reading of the 96 wells, and exiting.

I. Variation of the Signal of a Cryptate Conjugate at 620 nm as a Function of the Serum The following are introduced into a 96-well white microplate (Dynatech, USA):

100 µl of test serum, and

200 µl of an anti-prolactin antibody/europium cryptate conjugate at a concentration of 0.5 µg/ml of antibody in 100 mM phosphate buffer, pH 7.5, HSA 1 g/l, NaF 150 mM.

The europium cryptate used is trisbipyridinediamine ($Eu^{3+}$), the preparation of which is described in European patent application 321 353 (Examples 3 and 4).

The anti-prolactin antibody used is the 3D3 antibody (CIS bio international, France).

The 3D3 antibody/europium cryptate conjugate is prepared as described in Example 1.

After incubation for 1 hour at 37° C., the fluorescence is detected at 620 nm by the time-resolved method with a measuring delay of 50 µs and an integration time of 400 µs. The measuring time is 1 s.

The optical density of the serum is measured at 310 nm with the aid of a Lambda 15 spectrophotometer from PERKIN ELMER (UK).

The results are reported in Table IV below:

TABLE IV

| Serum | OD at 310 nm | Signal at 620 nm |
|---|---|---|
| 1 | 0.66 | 25,693 |
| 2 | 3.3 | 7,754 |
| 3 | 0.33 | 33,156 |
| 4 | 0.90 | 24,959 |

These results show that the measured signal varies greatly as a function of the optical density of the serum.

Under these conditions, it is impossible to perform a reliable assay because the result depends not only on the quantity of analyte in the serum but also on the optical quality of the serum.

II. Correction of the Signal of the Acceptor

An immunoassay is then performed by successively introducing the following into the microplate:

100 µl of serum,

100 µl of anti-prolactin 3D3 monoclonal antibody/europium cryptate trisbipyridinediamine ($Eu^{3+}$) conjugate at a concentration of 0.5 µg/ml of antibody in the above phosphate buffer, and 100 µl of anti-prolactin $E_1$ monoclonal antibody/allophycocyanin conjugate at a concentration of 3.5 µg/ml of antibody in the same buffer.

This $E_1$ antibody (CIS bio international, France)/ allophycocyanin (Cyanotech, USA) conjugate is prepared as described in Example 1.

The measurement is made at 665 nm and the measured value is corrected by dividing this value by the value of the fluorescence measured at 620 nm, which reflects the optical properties of the medium.

The values of concentrations determined with the aid of a calibration curve as indicated in Example 1, with or without correction, are compared with the values obtained by using the ELSA-PRL radioimmunometric assay kit (CIS bio international, France) as a reference.

The results are reported in Table V below, which shows the values of the prolactin concentrations, expressed in μU/ml, determined respectively by the ELSA-PRL assay (ELSA) and by measurement of the fluorescence at 665 nm without correction ($FIA_{665}$) and with correction ($FIA_{665/620}$), as well as the value of the fluorescence measured for the different samples at 620 nm ($FLUO_{620}$), expressed in counts per second.

TABLE V

| Sample no. | ELSA | $FIA_{665/620}$ | $FIA_{665}$ | $FLUO_{620}$ |
|---|---|---|---|---|
| 1 | 358 | 394 | 195 | 42,148 |
| 2 | 530 | 592 | 91 | 28,272 |
| 3 | 65 | 92 | 18 | 40,495 |
| 4 | 153 | 178 | 94 | 43,363 |
| 5 | 251 | 289 | 86.7 | 38,007 |
| 6 | 161 | 146 | 86.4 | 44,531 |
| 7 | 179 | 189 | 77 | 40,873 |
| 8 | 285 | 297 | 161 | 41,403 |
| 9 | 310 | 330 | 106 | 35,214 |
| 10 | 2744 | 3427 | 1470 | 31,670 |
| 11 | 196 | 153 | 15 | 36,551 |
| 12 | 244 | 198 | 55 | 38,134 |
| 13 | 447 | 477 | 300 | 40,340 |
| 14 | 251 | 234 | 350 | 58,615 |

These results confirm the variability of the measured signal as a function of the serum sample assayed.

In fact, given that the antibody/cryptate conjugate is present in excess in the assay, compared with the target analyte, the signal measured at 620 nm (which corresponds to the conjugate not forming part of the complex) should be constant.

Furthermore, it is pointed out that the values of prolactin concentrations determined from the measurement of the signal at 665 nm ($FIA_{665}$) do not correspond to the values obtained by the reference assay, whereas the values obtained by the corrected measurement ($FIA_{665/620}$) correlate well with the latter.

Figure 2:
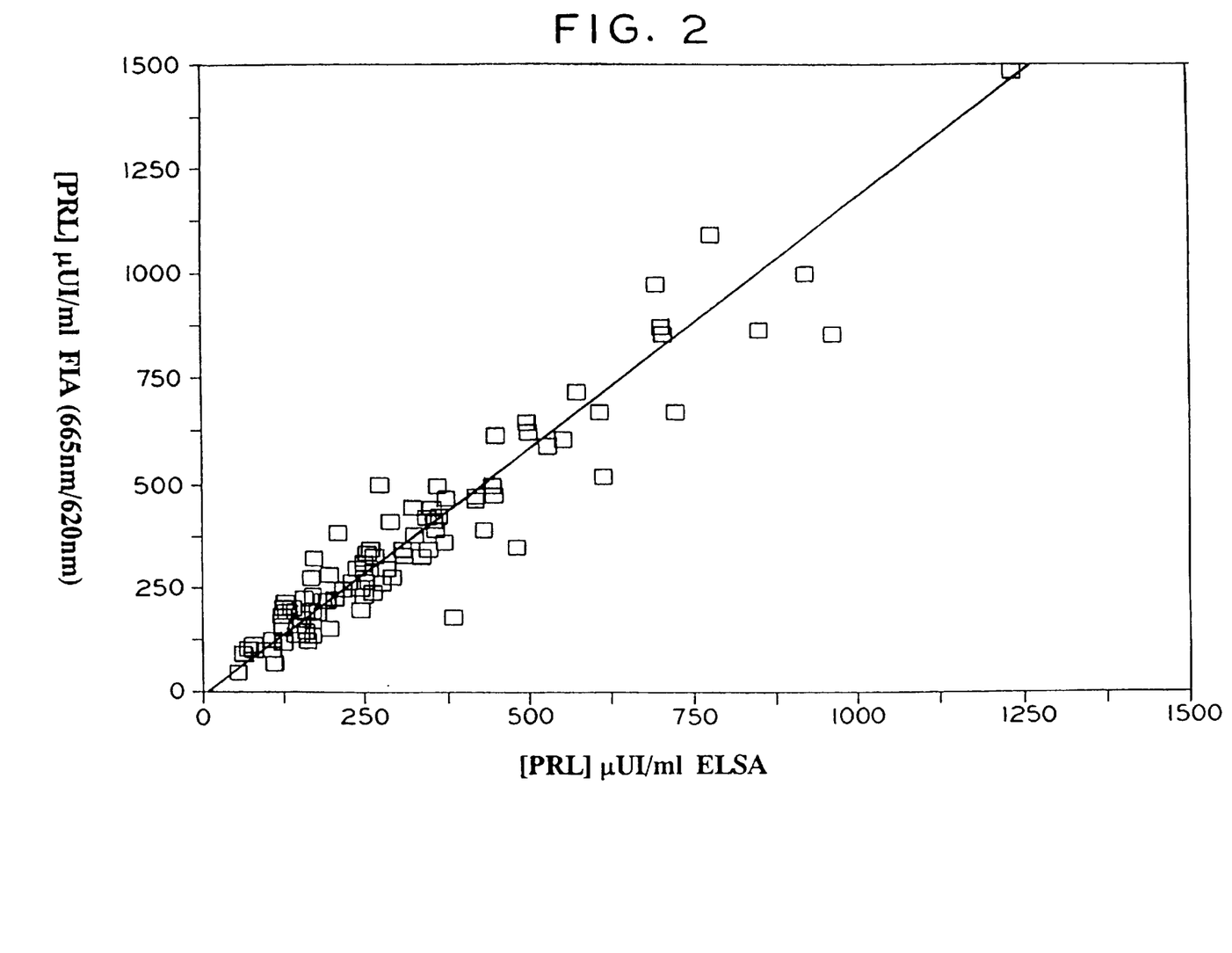
FIG. 2 is a graph in which the abscissa shows the prolactin concentration determine by the ELSA-PRL test in UI/ml and ordinates shows the concentration determine by a corrected measurement.
Figure 3:
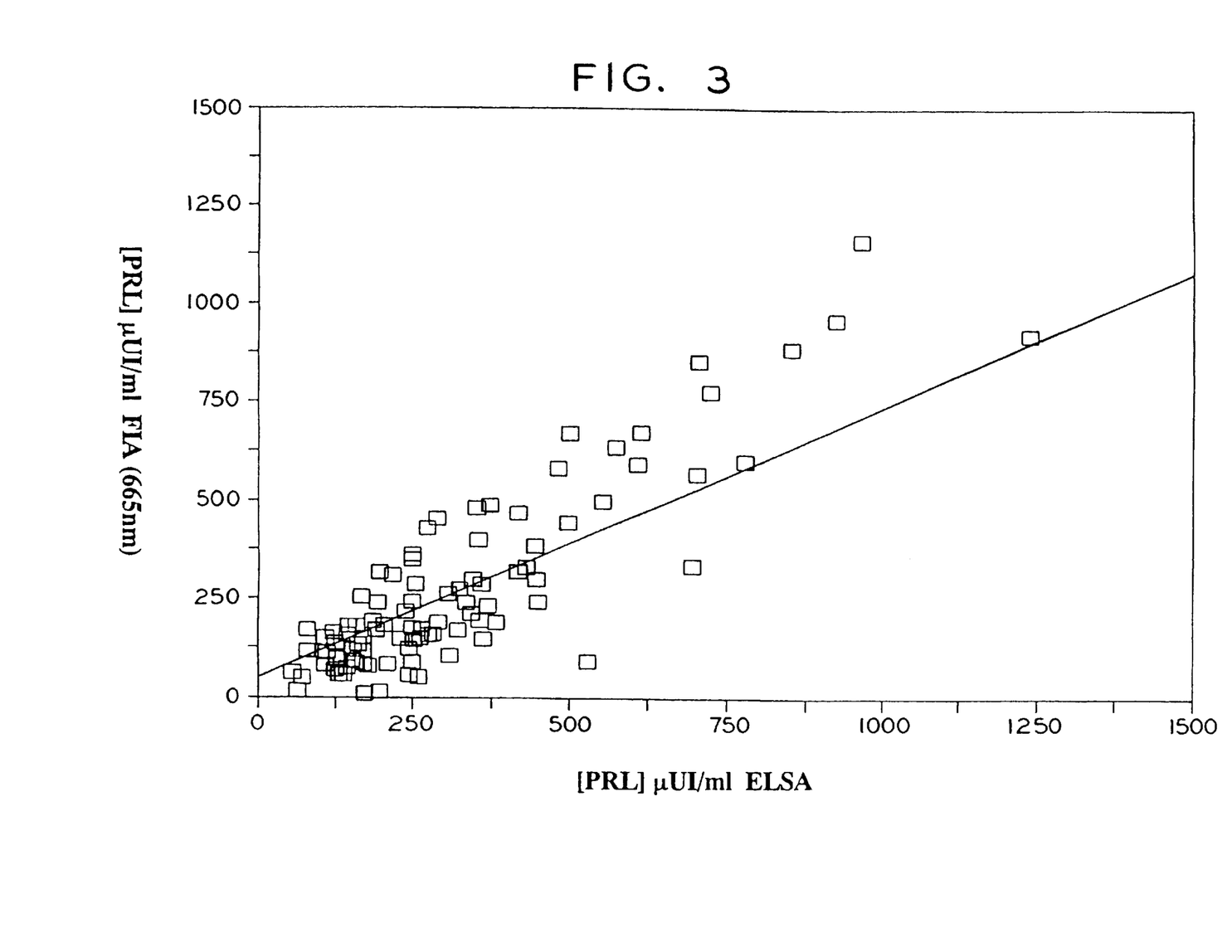
FIG. 3 is a graph similar to the graph illustrated in FIG. 2 in which the abscissa is the same as FIG. 2 and the ordinate shows an uncorrected measurement.

This correlation is illustrated by the curves of FIGS. 2 and 3, in which the abscissa shows the prolactin concentration determined by the ELSA-PRL test, in IU/ml, and the ordinate respectively shows the concentration determined by the corrected measurement $FIA_{665/620}$ (FIG. 2) or by the uncorrected measurement $FIA_{665}$ (FIG. 3), expressed in IU/ml.

The results obtained on 97 sera show that the correlation is obtained only with correction of the signal measured at 665 nm.

What is claimed is:

1. A photometric system for correcting the variations of luminescence due to the optical properties of a measuring medium in a luminescent method of detecting or determining a target analyte in said measuring medium, said system comprising:
    (a) an exciting light, source for irradiating a luminescent assay, wherein said assay upon excitation emits luminescence at two different wavelengths $\lambda_1$ and $\lambda_2$;
    (b) means for containing said assay, wherein said means for containing said assay is spaced apart from said light source to form a gap therebetween;
    (c) means for splitting the luminescence emitted by the assay at wavelengths $\lambda_1$ and $\lambda_2$ following excitation, wherein the luminescence at $\lambda_1$ is emitted by a reference compound and reflects the optical properties of the medium, and the luminescence at $\lambda_2$ is emitted by a tracer compound and is proportional to the amount of analyte;
    (d) means for collecting the luminescence emitted at wavelength $\lambda_1$ and $\lambda_2$; and
    (e) means for measuring the luminescence emitted at wavelength $\lambda_2$ and correcting said emission on the basis of the luminescence emitted at $\lambda_1$.

2. The system of claim 1 further comprising a built-in method of correcting the measurement of the luminescent emission made at wavelength $\lambda_2$, consisting of fixing a counting rate on a channel measuring the luminescent emission of the reference compound at wavelength $\lambda_1$, and then, when this counting rate is reached, triggering the end of the measurement on a channel measuring the luminescent emission at wavelength $\lambda_2$.

3. The system of claim 1 wherein the luminescence emitted at $\lambda_2$ results from an energy transfer.

4. The system of claim 1 wherein the luminescence emitted by the reference compound and by the tracer compound, at wavelengths $\lambda_1$ and $\lambda_2$ respectively, are measured simultaneously.

5. The system of claim 1 wherein a corrected luminescence is calculated by dividing the luminescence at $\lambda_2$ by the luminescence at $\lambda_1$ to obtain the corrected luminescence.

6. The system of claim 1 wherein the tracer compound and the reference compound are the same compound.

7. The system of claim 1 wherein the tracer compound and the reference compound are different compounds.

8. The system of claim 1 wherein the tracer compound and/or the reference compound are flourescent compounds.

9. The system of claim 1 wherein the tracer compound and/or the reference compound are rare earth chelates or cryptates.

10. The system of claim 1 wherein the measurement of the luminescent emission at wavelength $\lambda_2$ is made by a time-resolved method.

11. The system of claim 1 wherein the emission lifetime of the tracer compound and/or of the reference compound are more than one microsecond.

12. The system of claim 1 wherein the corrected luminescence is measured with a picomol/liter measuring sensitivity.

13. The system of claim 1 further comprising a lens focusing an exciting beam from said light source to said assay.

14. The system of claims further comprising means for loading the means for containing the assay, positioning said means for containing the assay under said light source, and allowing automatic sequential reading of luminescence emitted by said assay.

15. The system of claim 1 further comprising means for directing the exciting light beam on the assay.

16. The system of claim 15 wherein said means for directing said exciting light beam on the assay is selected from the group consisting of filters and lenses.

17. The system of claim 1 wherein said means for containing said assay are selected from the group consisting of plates, microplates, and wells.

18. The system of claim 1 wherein said means for collecting the luminescence is selected from the group consisting of lenses and filters.

19. A photometric system for correcting the variations of luminescence due to the optical properties of the measuring medium in a luminescent method of detecting or determining a target analyte in said measuring medium, said system comprising:

(a) an exciting light source for irradiating a luminescent assay, wherein said assay upon excitation emits luminescence at two different wavelengths $\lambda_1$ and $\lambda_2$;

(b) a container for containing said assay wherein said container is spaced apart from said light source to form a gap therebetween;

(c) one or more filters for splitting the luminescence emitted by the assay at wavelengths $\lambda_1$ and $\lambda_2$ following excitation, wherein the luminescence at $\lambda_1$ is emitted by a reference compound and reflects the optical properties of the medium, and the luminescence at $\lambda_2$ is emitted by a tracer compound and is proportional to the amount of analyte;

(d) one or more photomultipliers for collecting the luminescence emitted at wavelength $\lambda_1$ and $\lambda_2$; and (e) means for measuring the luminescence emitted at wavelength $\lambda_2$ and correcting said emission on the basis of the luminescence emitted at $\lambda_1$.

* * * * *

UNITED STATES PATENT AND TRADEMARK OFFICE
CERTIFICATE OF CORRECTION

PATENT NO. : 6,352,672 B1
DATED : March 5, 2002
INVENTOR(S) : Michel Mabile, Gerard Mathis, Etienne Jean-Pierre Jolu, Dominique Pouyat and Christopher Dumont It is certified that error appears in the above-identified patent and that said Letters Patent is hereby corrected as shown below:

<u>Column 8,</u>
Line 61, change "E280nm" to read -- $\varepsilon$280m --

<u>Column 14,</u>
Line 52, "claims" should read -- claim --
Line 52, after "claims" -- 1 --

Signed and Sealed this

Twentieth Day of August, 2002

Attest:

JAMES E. ROGAN
Attesting Officer
Director of the United States Patent and Trademark Office